US011170500B1

(12) United States Patent
Jones et al.

(10) Patent No.: US 11,170,500 B1
(45) Date of Patent: Nov. 9, 2021

(54) PYRAMID IMAGE QUALITY INDICATOR (IQI) FOR X-RAY COMPUTED TOMOGRAPHY

(71) Applicant: United States of America as represented by the Administrator of NASA, Washington, DC (US)

(72) Inventors: Justin Jones, Greenbelt, MD (US); Antonio Moreno, Greenbelt, MD (US); Olivia Landgrover, Greenbelt, MD (US)

(73) Assignee: United States of America as represented by the Administrator of NASA, Washington, DC (US)

( * ) Notice: Subject to any disclaimer, the term of this patent is extended or adjusted under 35 U.S.C. 154(b) by 116 days.

(21) Appl. No.: 16/583,336

(22) Filed: Sep. 26, 2019

Related U.S. Application Data

(60) Provisional application No. 62/758,156, filed on Nov. 9, 2018.

(51) Int. Cl.

| | |
|---|---|
| ***A61B 6/00*** | (2006.01) |
| ***G06T 7/00*** | (2017.01) |
| ***G01T 7/00*** | (2006.01) |
| ***G01T 1/17*** | (2006.01) |

(52) U.S. Cl.
CPC .............. *G06T 7/0012* (2013.01); *G01T 1/17* (2013.01); *G01T 7/005* (2013.01); *G06T 2207/10081* (2013.01); *G06T 2207/30168* (2013.01)

(58) Field of Classification Search
CPC ......... G06T 7/0012; G06T 2207/10081; G06T 2207/30168; G01T 7/005; G01T 1/17; A61B 6/58; A61B 6/581; A61B 6/583; A61B 6/585
See application file for complete search history.

(56) References Cited

U.S. PATENT DOCUMENTS 4,055,771 A * 10/1977 Goodenough ......... A61B 6/583 378/18
5,056,130 A * 10/1991 Engel ..................... A61B 6/035 378/207
5,841,835 A * 11/1998 Aufrichtig ............... H05G 1/26 378/207
6,231,231 B1 * 5/2001 Farrokhnia ............ A61B 6/583 378/204
9,924,920 B2 * 3/2018 Gay ..................... G01N 23/046
10,395,560 B2 * 8/2019 Groenewald .......... A61B 6/583
10,871,591 B2 * 12/2020 Atherton ................ G01V 5/005

* cited by examiner

*Primary Examiner* — Jurie Yun
(74) *Attorney, Agent, or Firm* — Matthew F. Johnston; Bryan A. Geurts; Helen M. Galus

(57) ABSTRACT

A three-dimensional image quality indicator suitable for assessing the quality of a CT scan includes a pyramidal structure having a base, an apex, and a plurality of triangular faces extending from the base to the apex; at least two grooves in each triangular face, each groove tapering from a wide end at the base to a narrow end at the apex; and a land between each pair of adjacent grooves in each triangular face, each land tapering from the base to the apex. When a two-dimensional slice is taken in a plane parallel to the base of the pyramidal structure, the grooves are observable at the edges of the structure. The smallest observable groove width provides a measure of CT resolution.

19 Claims, 4 Drawing Sheets

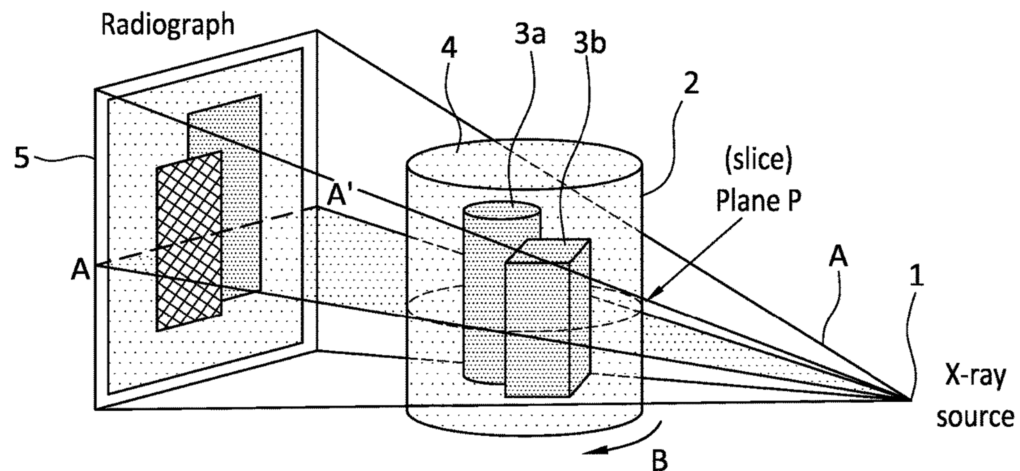
FIG. 1 (Prior Art)
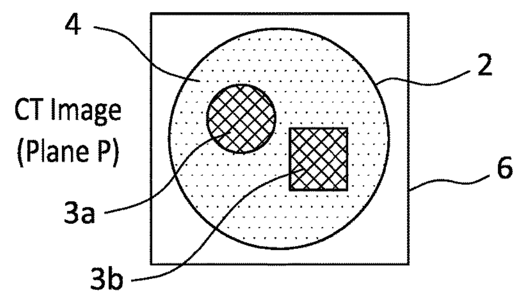
FIG. 1A (Prior Art)
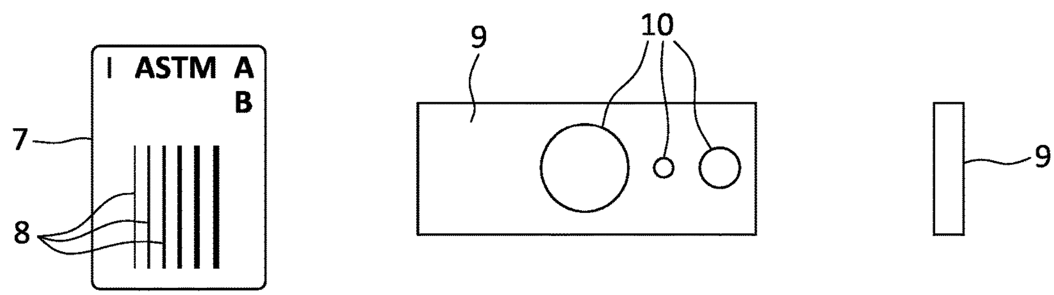
FIG. 2 (Prior Art)
FIG. 3 (Prior Art)
FIG. 3A (Prior Art)

PYRAMID IMAGE QUALITY INDICATOR (IQI) FOR X-RAY COMPUTED TOMOGRAPHY

CROSS-REFERENCE TO RELATED APPLICATIONS

This application claims the benefit of U.S. Provisional Patent Application No. 62/758,156 entitled "PYRAMID IMAGE QUALITY INDICATOR (IQ) for X-ray Computed Tomography," filed Nov. 9, 2018, and is hereby incorporated herein by reference in its entirety.

STATEMENT REGARDING FEDERALLY SPONSORED RESEARCH OR DEVELOPMENT

The invention described herein was made in part by employees of the United States Government and may be manufactured and used by or for the Government of the United States of America for governmental purposes without the payment of any royalties thereon or therefor.

FIELD

This invention relates generally to image quality indicators for X-ray scans of three-dimensional objects.

BACKGROUND

Computed tomography (CT) is a powerful radiographic method that provides a versatile inspection technique whenever the primary goal is to quantify volumetric features in three dimensions. Since the method is based on x-rays, it applies equally well to parts that are metallic or nonmetallic, solid or porous, smooth or irregularly surfaced. It is also useful for articles having simple geometries or complex geometries.

To ensure radiographic image quality when X-ray measurements are made, image quality indicators (IQIs) are used. A good IQI should show allow the user to determine the minimum resolution and contrast that is reliably observable with the X-ray system.

A suitable IQI for a CT scan of a three-dimensional object would be in the form of a representative quality indicator, or RQI, with a similar geometry to the three-dimensional object, and would be made from a radiologically similar material. However, this level of customization is not always an option, so more generalized IQIs of a convenient geometry are commonly used.

SUMMARY

The present disclosure is directed to improved three-dimensional image quality indicators. A brief summary of various embodiments disclosed herein is presented. Detailed descriptions of various embodiments adequate to allow those of ordinary skill in the art to make and use the inventive concepts will follow in later sections.

Various embodiments disclosed herein relate to a three-dimensional image quality indicator, including a pyramidal structure having a base, an apex, and a plurality of triangular faces extending from the base to the apex; at least two grooves in each triangular face, each groove tapering from a wide end at the base to a narrow end at the apex; and a land between each pair of adjacent grooves in each triangular face, with each land tapering from the base to the apex. In various embodiments, the pyramidal structure may have a truncated apex with a flat or rounded surface, or a pointed apex.

In various embodiments, each groove in each pyramidal face has straight edges and a defined width at half-height, where "width at half-height" refers to 50% of the height of the pyramidal structure.

In various embodiments, each groove on a first triangular face has straight edges and a first defined width at half-height; and each triangular face which is adjacent to the first triangular face, e.g., each triangular face which contacts the first triangular face at an edge, has grooves with straight edges and a second defined width at half-height. In various embodiments, the second defined width at half-height is different from the first defined width at half-height. In various embodiments, the three-dimensional image quality indicator has an even number of triangular faces, the even number ranging from 4 to 8, so that a first group of alternating faces have grooves with the first defined width at half-height; and a second group of alternating faces have grooves with the second defined width at half-height. In various embodiments, the pyramidal structure has 4 triangular faces, where:

- a first face and a third face have grooves with the first defined width at half-height, where the first and third faces are non-adjacent; and
- a second face and a fourth face have grooves with the second defined width at half-height, where the second and fourth faces are non-adjacent.

In various embodiments, each groove on each triangular face has straight edges and a defined width at half-height; and no two triangular faces have grooves with the same defined width at half-height. In various embodiments, the pyramidal structure has from 3 to 8 triangular faces, e.g., four triangular faces.

In various embodiments, the three-dimensional image quality indicator may further include a conical bore in the pyramidal structure, with the conical bore having a first diameter at the base and a second diameter at the apex, the first diameter being greater than the second diameter. A stack comprising a plurality of cylindrical members may be configured to occupy the conical bore, wherein at least one of the cylindrical members has a plurality of holes therethrough. In various embodiments, at least one of the cylindrical members is a radiographic penetrameter having a plurality of holes of varying diameter therethrough.

In various embodiments, the three-dimensional image quality indicator includes a first pair of adjacent triangular faces which may contact at a first edge, and the first edge may include a plurality of evenly spaced features, e.g., notches.

Various embodiments disclosed herein relate to a method of determining a resolution obtainable in a cross sectional image of a three-dimensional object obtained by computed tomography, by:

- obtaining a series of cross sectional images of a pyramidal structure having a base, an apex, and a plurality of triangular faces extending from the base to the apex, each cross sectional image being along a plane parallel to the base, wherein each triangular face has at least two grooves and a land between each pair of adjacent grooves, with each groove tapering from a wide end at the base to a narrow end at the apex; and
- observing the series of cross sectional images to determine a minimum resolvable groove width for the grooves on the triangular faces. In various embodiments, each groove tapers from a width of 0.5 mm to 4 mm at the wide end to a width of 0.005 mm to 0.5 mm at the narrow end, or 0.5 mm to 4 mm at the wide end to a width of 0.01 mm to 0.1 mm at the narrow end.

The pyramidal structure may be formed by 3D printing, or additive manufacturing, from a CAD file, allowing multiple IQIs of varying sizes to be prepared by increasing or decreasing the absolute dimensions of the CAD file. The absolute dimensions of the CAD file may be increased without changing relative dimensions between parts.

In various embodiments, each groove is characterized in that a ratio of a width of the narrow end of the groove to a width of the wide end of the groove is between 1:10 and 1:100, between 1:12.5 and 1:60, or between 1:15 and 1:32.

Various embodiments disclosed herein relate to a method of determining a contrast obtainable in a cross sectional image of a three-dimensional object obtained by computed tomography, by obtaining a series of cross sectional images of a pyramidal structure having a bore and at least one disc-shaped penetrameter positioned within the bore. In various embodiments, the cross sectional images pass through the disc-shaped penetrameter. Each penetrameter may have a plurality of holes of varying sizes, and the series of cross sectional images are observed to determine the smallest penetrameter hole detectable to determine the minimum observable contrast.

BRIEF DESCRIPTION OF THE DRAWINGS

In order to better understand various exemplary embodiments, reference is made to the accompanying drawings, wherein:

FIG. 1 shows the process of obtaining a CT scan;

FIG. 1A shows a two-dimensional slice of a three-dimensional CT scan obtained by the process of claim 1;

FIGS. 2 and 3 show two-dimensional image quality indicators;

FIG. 3A shows a side view of the two-dimensional quality indicator of FIG. 3.

DETAILED DESCRIPTION

Figure 4:
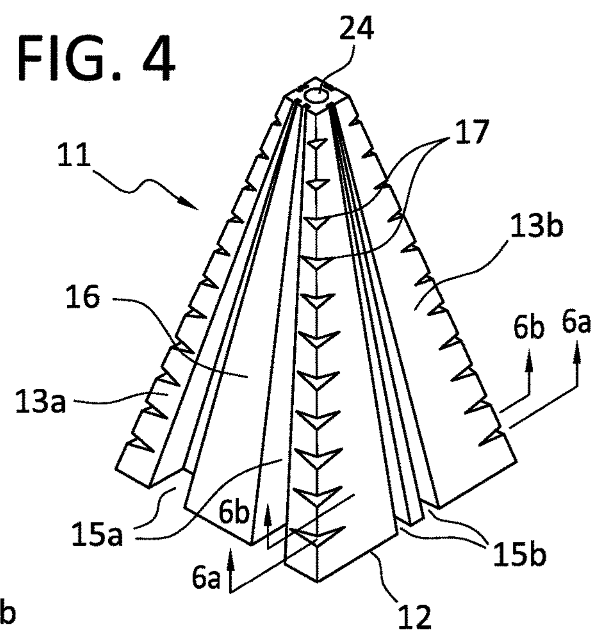
FIG. 4 shows a three-dimensional image quality indicator as disclosed herein.

Referring now to the drawings, in which like numerals refer to like components or steps, there are disclosed broad aspects of various exemplary embodiments.

Computed tomography (CT) is a powerful radiographic method that provides a versatile inspection technique whenever the primary goal is to quantify volumetric features in three dimensions. In addition, since the method is based on x-rays, it applies equally well to parts that are metallic or nonmetallic, solid or porous, smooth or irregularly surfaced, or simple or complex shaped. Computed tomography is illustrated in FIG. 1.

An object 2 may contain a matrix material 4 and embedded components or structural features 3*a* and 3*b*. An X-ray source 1 passes a plurality of X-rays A through object 2. A single radiograph 5 may be obtained, containing a single two-dimensional image of object 2. In radiograph 5, information on a slice plane P parallel to X-rays from source 1 projects into a single line, A-A', so that three-dimensional relationships between features 3*a* and 3*b* are not yet known. In CT, object 2 may be rotated in the direction of arrow B in a plurality of steps, with a separate X-ray radiograph being obtained after each rotational step. A CT scan is thus derived from a large number of radiographs 5 obtained from systematic observations at different viewing angles, and a 3D image may be reconstructed from the radiographs with the aid of a computer.

As shown in FIG. 1A, a two-dimensional CT image 6 in a plane P, where plane P is perpendicular to each radiograph 5 obtained as in FIG. 1, may be obtained from the 3D image. Image 6 shows the arrangement of matrix material 4 and embedded components or structural features 3*a* and 3*b* within object 2.

To ensure radiographic image quality when RT and CT measurements are made, image quality indicators (IQIs) are used. An IQI may show the effect of changing resolution, contrast, and/or noise on image quality. Commercially available IQIs include IQIs 7, where IQI 7 includes a plurality of wires 8 of varying thickness, as shown in FIG. 2. Some IQIs include IQIs 9, where IQI 9 includes a plurality of holes 10 of varying diameter, as shown in FIG. 3. The diameter of the thinnest wire that can be seen in a wire IQI 7 or a hole in IQI 9 provides a measure of the sensitivity in a radiographic image. In some IQIs, a plurality of paired wires are used, with each set of paired wires being separated by a different distance. The smallest line distance between a pair of wires that can be separated in an IQI provides a measure of the radiographic resolution. Such IQIs are typically flat, as shown for IQI 9 in FIG. 3A.

However, CT systems perform a geometric reconstruction using up to 360 degrees of incident angles. Conventional flat IQIs offer an unrealistic basis for an IQI for a three-dimensional image unless the inspected part is also flat. Since parts inspected by CT often are not flat and may be geometrically complex with intricate internal features or deeply embedded defects in critical regions, IQIs that are more sophisticated are needed. IQIs with a three-dimensional structure would be useful in the aerospace industry as well as other industries that use CT to analyze parts with a complex shape, e.g., industries which manufacture parts for automotive, medical, and consumer products.

To ensure inspection accuracy over the range of incident angles used, CT IQIs may be radially symmetric, e.g., they may be disks, cylinders, cones, or pyramids. CT IQIs may also be shaped as a regular polygon having from 3 to 8 sides, with a constant cross sectional area, e.g., a cube, or a variable cross sectional area, e.g., a pyramid.

Three-dimensional IQIs with a variable cross sectional area, e.g., a large end and a small end, have the advantage that a single IQI may be used to calibrate a CT image for parts of different sizes. If a CT image of a large part is needed, a two-dimensional CT image 6 of a large end of an IQI may be obtained and used to assess image quality. If a CT image of a small part is needed, a two-dimensional CT image 6 of a small end of an IQI may be used to assess image quality.

Figure 4A:
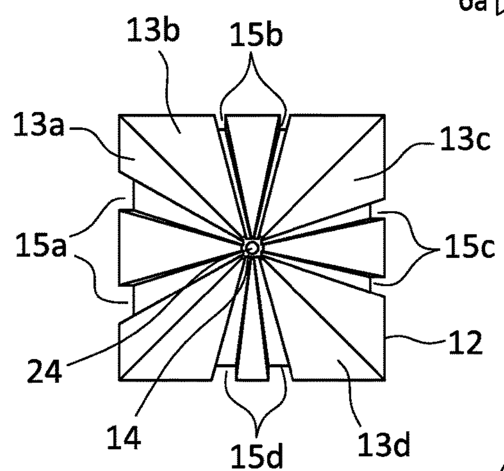
FIG. 4A shows a top plan view of the three-dimensional image quality indicator of FIG. 4.
Figure 4B:
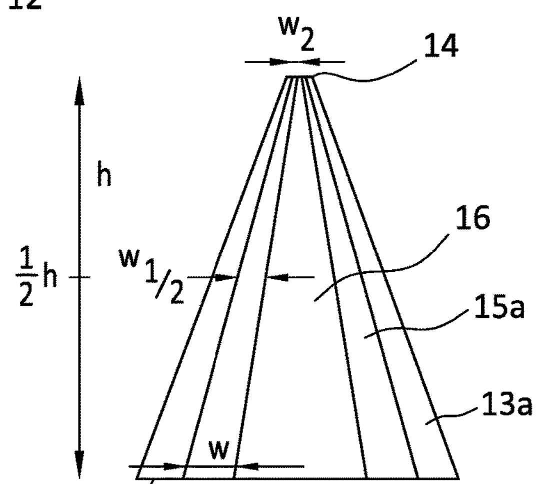
FIG. 4B shows a front elevational view of the three-dimensional image quality indicator of FIG. 4.

FIG. 4 is a perspective view showing a three-dimensional image quality indicator as disclosed herein. The image quality indicator may be a pyramidal structure 11 with a base 12, an apex 14, and a plurality of triangular faces. A first triangular face 13*a* has at least two grooves 15*a* therein, where grooves 15*a* have straight edges and taper from a first width $w_1$ at base 12 to a second width $w_2$ at apex 14, as shown in the side view of pyramidal structure 11 in FIG. 4B. Each pair of adjacent grooves are separated by a land 16, with each land tapering from the base to the apex. Grooves 15*a* have a first defined width $w_{1/2}$ at half height, where width at half height is the groove width at 50% of the pyramid height. Width $w_{1/2}$ at half height may be defined as $w_{1/2}=(w_1-w_2)/2$, where groove width tapers at a constant rate. A second triangular face 13*b* has at least two grooves 15*b* therein, where grooves 15*b* taper from a first width at base 12 to a second width at apex 14, and have a second defined width $w_{1/2}$ at half height. In various embodiments, the pyramid may have from 3 to 8 sides, an even number of sides ranging from 4 to 8 sides, or 4 sides. In various embodiments, the pyramidal structure may have a truncated apex with a flat or rounded surface, as seen in FIG. 4, or a pointed apex. In various embodiments, the interior of the pyramidal structure may include a conical bore 24, with an opening to bore 24 within pyramidal structure 11 being visible at the apex 14 (conical bore 24 may also be seen in FIG. 7C). In various embodiments, the pyramidal structure 11 may have four faces, including face 13*a*, face 13*b*, a third triangular face 13*c* with at least two grooves 15*c* therein, and a fourth triangular face 13*d* with at least two grooves 15*d* therein, as shown in FIG. 4A. For ease of reference, the following disclosure may refer to a face 13, where face 13 may be any one of faces 13*a*, 13*b*, 13*c*, and 13*d*. Also, the following disclosure may refer to faces 13, where faces 13 may be two or more of faces 13*a*, 13*b*, 13*c*, and 13*d*.

In various embodiments, each groove in each pyramidal face has straight edges and a defined width at half-height, where "width at half-height" refers to the groove width at 50% of the height of the pyramidal structure.

In various embodiments, each groove on a first triangular face 13*a* has straight edges and a first defined width at half-height; and each triangular face which is adjacent to the first triangular face 13*a*, e.g., each triangular face which contacts the first triangular face at an edge 25, also has grooves with straight edges and a second defined width at half-height. In various embodiments, the second defined width at half-height is different from the first defined width at half-height. In various embodiments, the three-dimensional image quality indicator has an even number of triangular faces, the even number ranging from 4 to 8, so that a first group of alternating faces have grooves with the first defined width at half-height; and a second group of alternating faces have grooves with the second defined width at half-height. In various embodiments, the pyramidal structure 11 has 4 triangular faces, where:

- a first face 13*a* and a third face 13*c* have grooves with the first defined width at half-height, where the first and third faces are non-adjacent; and
- a second face 13*b* and a fourth face 13*d* have grooves with the second defined width at half-height, where the second and fourth faces are non-adjacent.

In various embodiments, grooves 15*a*, 15*b*, 15*c*, and 15*d* in FIG. 4A may have the same width at half-height. In various embodiments, grooves 15*a*, 15*b*, 15*c*, and 15*d* in FIG. 4A may have different widths at half-height. In various embodiments, all grooves on a single face 13 may have the same width at half-height. In various embodiments, multiple grooves of varying width may be present on a single face 13. In various embodiments, each face 13 has at least two grooves with a defined width at half-height therein, with the proviso that no two faces have grooves with the same defined width at half-height, i.e., each of faces 13*a*, 13*b*, 13*c*, and 13*d* has grooves with a different width.

In various embodiments, the pyramidal structure has a plurality of faces 13, with each face 13 having two edges 25. Each face 13 contacts two adjacent faces at edges 25. The grooves on a first face 13 may have a first width at half-height, and each face contacting the first face may have grooves with a second width at half-height, where the second width is less than the first width. In various embodiments, the pyramidal structure may have an even number of faces 13, e.g., 4, 6, or 8 faces, with:

- a first set of even-numbered alternating faces, e.g., a second face 13*b* and a fourth face 13*d* in a four-sided pyramid as shown in FIG. 4A, each even-numbered face having grooves with a first width at half-height; and
- a second set of odd-numbered alternating faces, e.g., a first face 13*a* and a third face 13*c*, each odd-numbered face having a second width at half-height, where the second width is less than the first width.

In various embodiments, each groove on each triangular face 13 has straight edges and a defined width at half-height; and no two triangular faces 13 have grooves with the same defined width at half-height. In various embodiments, the pyramidal structure has from 3 to 8 triangular faces, e.g., four, five, or six triangular faces.

In various embodiments, the pyramidal structure 11 has 4 triangular faces 13 having a pair of grooves thereon, where each pair of grooves has a different groove width at half-height $w_{1/2}$. Such a pyramidal structure 11 may have:

a first face 13*a* with two grooves 15*a* thereon, where each groove 15*a* has a width $w_{1/2,A}$;

a second face 13*b* with two grooves 15*b* thereon, where each groove 15*b* has a width $w_{1/2,B}$, where $w_{1/2,B}<w_{1/2,A}$;

a third face 13*c* with two grooves 15*c* thereon, where each groove 15*c* has a width $w_{1/2,C}$, where $w_{1/2,B}<w_{1/2,C}<w_{1/2,A}$; and a fourth face 13*d* with two grooves 15*d* thereon, where each groove 15*d* has a width $w_{1/2,D}$, where $w_{1/2,B}<w_{1/2,D}<w_{1/2,C}$.

Figure 7A:
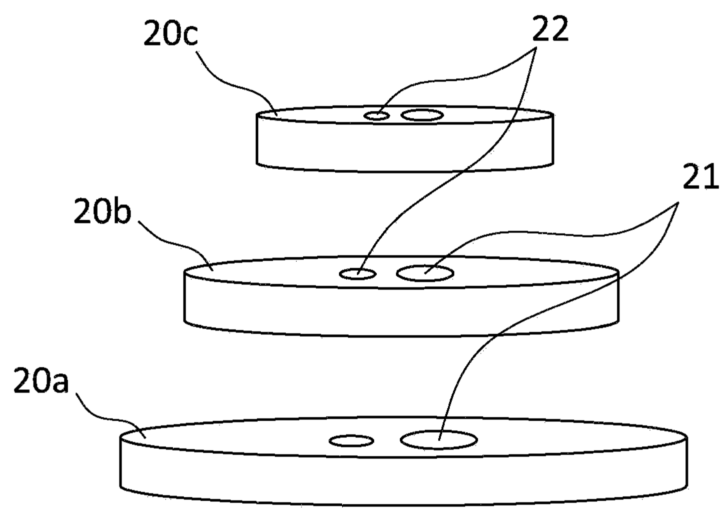
FIG. 7A shows a set of disc-shaped X-ray penetrameters.
Figure 7B:
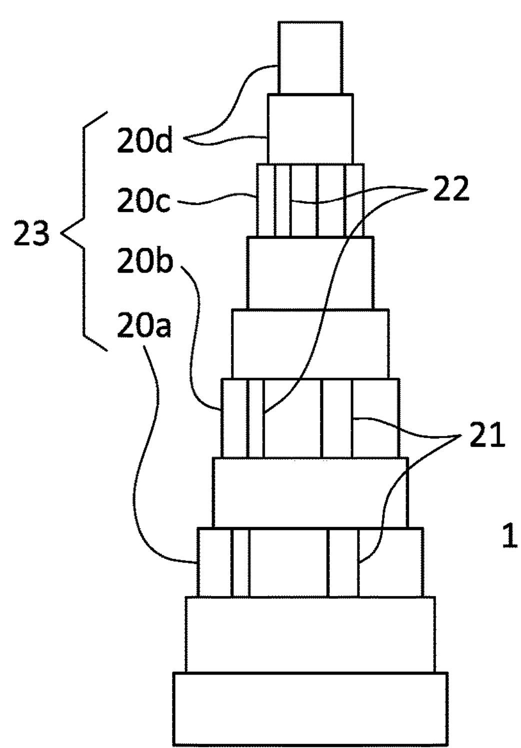
FIG. 7B shows a stack of disc-shaped elements, including the disc-shaped X-ray penetrameters of FIG. 7A.
Figure 7C:
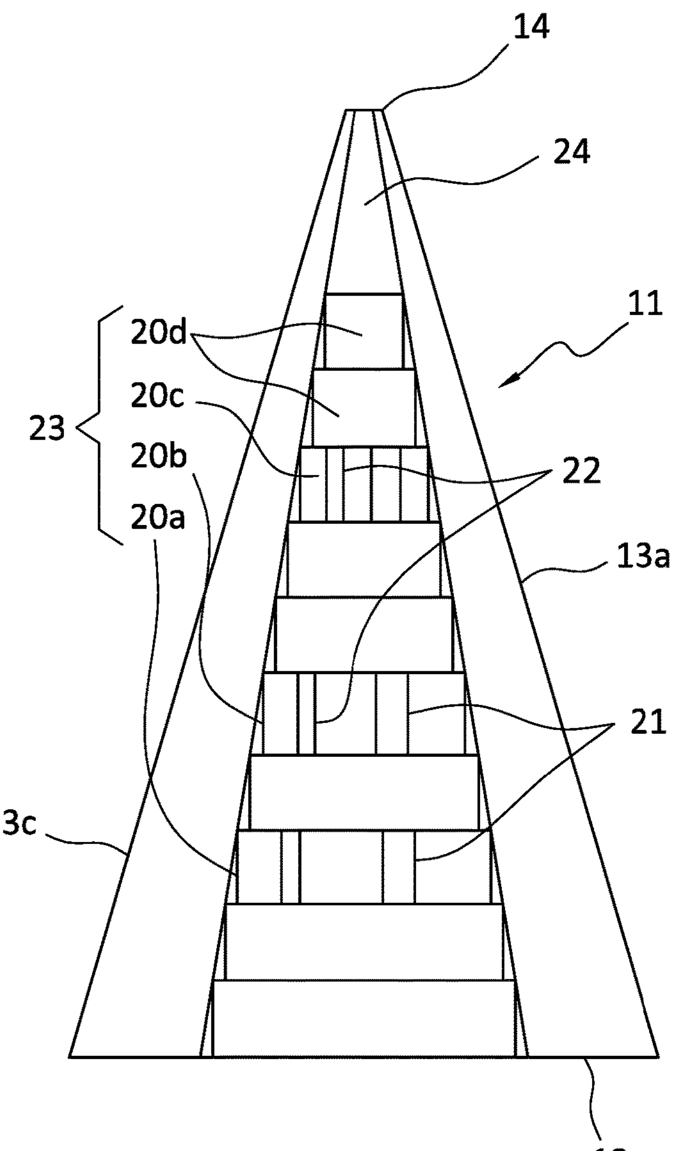
FIG. 7C shows the stack of FIG. 7B in a conical bore in a three-dimensional image quality indicator of FIG. 4.

In various embodiments, the three-dimensional image quality indicator may include a conical bore 24 in the pyramidal structure 11, visible at the apex of structure 11 in FIG. 4 and in FIG. 7C. The conical bore may have a first diameter at the base and a second diameter at the apex, the first diameter being greater than the second diameter.

In various embodiments, the three-dimensional image quality indicator may include a pyramidal structure 11 with a first pair of adjacent triangular faces 13 which may contact at a first edge 25, and the first edge 25 may include a plurality of evenly spaced features, e.g., notches 17, as shown in FIG. 4. In various embodiments, the pyramidal structure 11 may include a plurality of edges 25 where adjacent faces 13 meet, where each edge 25 includes a plurality of evenly spaced features, e.g., notches 17.

Various embodiments disclosed herein relate to a method of determining a resolution obtainable in a cross sectional image of a three-dimensional object obtained by computed tomography, by:

obtaining a series of cross sectional images of a pyramidal structure having a base, an apex, and a plurality of triangular faces extending from the base to the apex, each cross sectional image being along a plane parallel to the base, wherein each triangular face has at least two grooves and a land between each pair of adjacent grooves, with each groove tapering from a wide end at the base to a narrow end at the apex; and observing the series of cross sectional images to determine a minimum resolvable groove width for the grooves on the triangular faces.

In various embodiments, each groove tapers from a width of 0.5 mm to 4 mm at the wide end to a width of 0.005 mm to 0.5 mm at the narrow end, or 0.5 mm to 4 mm at the wide end to a width of 0.01 mm to 0.1 mm at the narrow end. In various embodiments, each groove may taper proportionately with a width of a face 13, so that at any point along the height of the pyramidal structure 11, the ratio of the width of face 13 to the width of the groove is constant.

Figure 5:
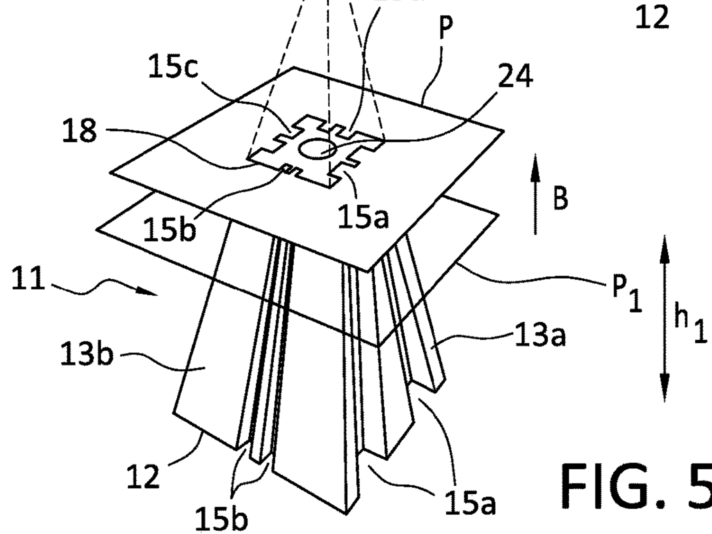
FIG. 5 shows a three-dimensional image quality indicator of FIG. 4, with a cross sectional area viewed in a slice in a plane P.

FIG. 5 is a second perspective view showing a three-dimensional image quality indicator as disclosed herein. The image quality indicator is a pyramidal structure 11 with a base 12 and four triangular faces 13. A first triangular face 13*a* has at least two grooves 15*a* therein, where grooves 15*a* taper from a first width $w_1$ at base 12 to a second width $w_2$ at an apex 14 (In FIG. 5, the portion of pyramidal structure 11 above plane P is shown with dashed lines). In various embodiments, the grooves on each face of pyramidal structure 11 have a half-height width which is different from the half-height width of the grooves on each of the remaining faces, e.g., grooves 15*b* on face 13*b* have a different width from grooves 15*a* on face 13*a*. As seen in FIG. 5, grooves 15*a* may be the widest grooves, and grooves 15*b* may be the narrowest grooves. A cross section of conical bore 24 may also be seen in FIG. 5.

A plurality of X-ray images from a variety of different directions may be used to calculate a three-dimensional representation of the structure of pyramidal structure 11 with a computer. The computer may also be used to calculate a cross section view 18 of the pyramidal structure 11 in plane P, as shown in FIG. 5. In FIG. 5, plane P is shown as being parallel to the plane of base 12. The cross section in plane P includes four pairs of grooves 15*a*, 15*b*, 15*c*, and 15*d*. The four pairs of grooves have varying width, from the widest grooves 15*a* to the narrowest grooves 15*b*. Each side of each groove 159 to 15*d* is resolvable in the cross section of plane P. Cross section views may be determined in different planes, e.g., plane $P_1$, which intersect pyramidal structure 11, and are parallel to plane P. As plane $P_1$ moves in the direction of arrow B, the width of each triangular face 13, as it intersects plane. $P_1$, decreases. The width of each groove 15*a* to 15*d*, as it intersects plane $P_1$, decreases proportionately. At some point as plane $P_1$ approaches apex 14 of pyramidal structure 11, grooves 15*a* to 15*d* will narrow to the point that the sides of the groove cannot be individually resolved in a CT scan. The minimum groove width at which the sides of a groove may be separately resolved provides a measure of the maximum resolution of the CT scan.

In various embodiments, each groove 15*a* to 15*d* tapers from a width of 0.5 mm to 4 mm at the wide end of pyramidal structure 11 to a width of 0.005 mm to 0.5 mm (5 to 500 microns) at the narrow end; or from a width of 0.5 mm to 4 mm at the wide end to a width of 0.01 mm to 0.1 mm (10 to 100 microns) at the narrow end. In various embodiments, grooves 15*a*, 15*b*, 15*c*, and 15*d* each have a different width at the wide end. For example, if each face 13 has a width of 16 to 24 mm at the base, grooves 15*b* may have a width of 0.5 mm to 1 mm at the wide end; grooves 15*d* may have a width of 1 mm to 2 mm at the wide end; grooves 15*c* may have a width of 2 mm to 4 mm at the wide end; and grooves 15*a* may have a width of 4 mm to 8 mm at the wide end. Increasing or decreasing the size of pyramidal structure 11 changes the width of each face 13. Increasing or decreasing the width of a face 13 allows the widths of grooves 15*a*, 15*b*, 15*c*, or 15*d* thereon to be increased or decreased proportionately.

A plurality of cross section slices of pyramidal structure 11 in a plurality of parallel planes $P_1$ may be taken, with each plane $P_1$ being a different height $h_1$ from base 12. As height $h_1$ increases, the distance between the walls of each groove 15*b* decreases. At some height, groove 15*b* is no longer observable, i.e., the walls of groove 15*b* are no longer separately resolvable. The distance between the walls of groove 15*b* at the maximum height, $h_{MAX}$, where the walls of groove 15*b* are separately observable is the maximum resolution of the CT apparatus. For example, at apex 14, shown as truncated in FIG. 5, grooves 15*b* may have a width of 10 microns and grooves 15*a* may have a width of 80 microns. If a CT scan showing a cross section of pyramidal structure 11 at the apex is able to resolve grooves 15*a* but not grooves 15*b*, then the resolution of the CT scan is greater than 80 microns but less than 10 microns; i.e., the smallest feature that can be observed by CI is sized between 10 microns and 80 microns.

Pyramidal structure 11 may be made from plastic or metal. Pyramidal structure 11 may be prepared by three-dimensional printing or additive manufacturing, using a photopolymer or from a metal such as stainless steel or a titanium alloy. Metal image quality indictors having a pyramidal structure may be prepared from metal using laser sintering or electron beam processes or micro laser sintering. Alternatively, pyramidal structure 11 may be machined from a metal or plastic block, or by prepared by lost wax molding. In various embodiments, pyramidal structure 11 may be prepared from a polymer by additive manufacturing, machining, or molding. In various embodiments, pyramidal structures 11 may be produced in multiple sizes by additive manufacturing, or 3D printing, using vector-based graphics files as digital source files. The size of the printed pyramidal structure 11 may be altered by scaling the size of the vectors in a digital source file to achieve a desired size of the printed structure.

Such 3D printing, or additive manufacturing, from a CAD file, allows multiple IQIs of varying sizes to be prepared by increasing or decreasing the absolute dimensions of the CAD file. The absolute dimensions of the CAD file may be increased without changing relative dimensions between parts. For example, the height of the pyramidal structure 11 and the width of each side of the base of the pyramid may be increased or decreased by a factor of two, without changing the shape of the pyramidal structure. Since relative dimensions are constant, while absolute dimensions may vary based on the desired size of an IQI, the grooves IS may be described in terms of a ratio of the width at the narrow end of the groove to a width of the wide end of the groove. Each groove may be characterized as having a ratio of a width of the narrow end to a width of the wide end between 1:10 and 1:100, between 1:12.5 and 1:60, or between 1:15 and 1:32.

The pyramidal structure may be prepared from a polymer and coated with a thin metal layer, e.g., a nickel or gold layer, by electroplating or electroless plating. The coating may assist in improving contrast, depending on x-ray power used. In various embodiments, the grooves 15*a* to 15*d* may be plated with a high-density metal layer, e.g., nickel, while the remainder of pyramidal structure 11 may be formed of a low-density polymer. In various embodiments, all surface areas of pyramidal structure 11, including grooves 15*sa* to

15*d*, faces 13, and conical bore 24, may be plated with a high-density metal layer, while the remainder of pyramidal structure 11 may be formed of a low-density polymer.

Figure 6A:
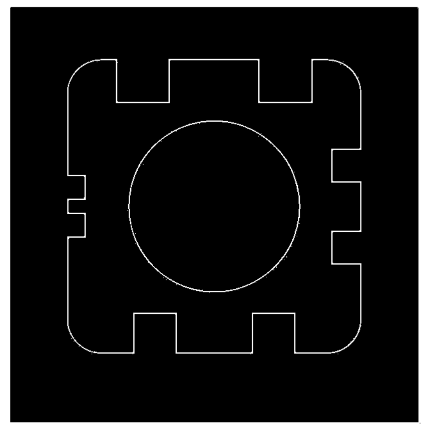
FIGS. 6A and 6B show two-dimensional slices of a CT scan of the three-dimensional image quality indicator of FIG. 4.
Figure 6B:
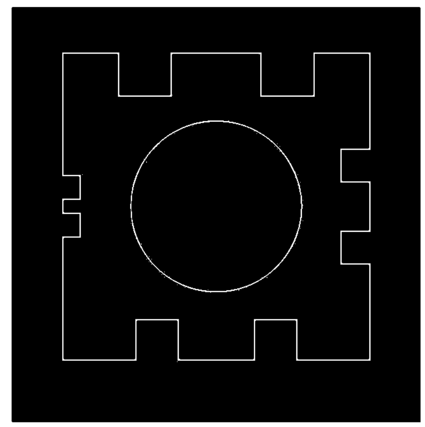

FIGS. 6A and 6B show CT scans of the image quality indicator of FIG. 4, with each scan being parallel to a base of pyramidal structure 11. The pyramidal structure 11 is made of a low-density plastic, with a high-density nickel plating on the outer surface of the pyramidal structure 11, including grooves 15*a* to 15*d* and conical bore 24 on the interior of pyramid 11. A first scan shown in FIG. 6A is taken as a slice through image quality indicator 11 of FIG. 4, in a plane defined by arrows 6*a*, where the plane of arrows 6*a* intersects pyramid 11 at notches 17. A second scan shown in FIG. 6B is taken as a slice through pyramidal structure 11 of FIG. 4, in a plane defined by arrows 6*b*.

Pyramidal structure 11 may be made of a plastic which does nor substantially absorb X-ray radiation, and shows up in a CT scan as a dark region with a notched square outer edge and a round inner edge, as seen in FIGS. 6A and 6B. If pyramidal structure 11 has an outer surface coated with an X-ray opaque metal plating, the metal plating 11 more heavily absorbs theX-ray radiation, and appear as a thin white line defining a square outer edge, where each side of the square has two notches therein, as seen in FIGS. 6A and 6B. If pyramidal structure 11 has a conical bore coated with an X-ray opaque metal plating, the metal plating the conical bore 24 of pyramidal structure 11 shows up as a circular inner edge of pyramidal structure 11. The slice of FIG. 6A includes notches 17, and has an outer boundary with sides which meet at curved edges, reflecting the shape of notches 17. The slice of FIG. 6B does not include notches 17 in the image quality indicator of FIG. 4 and has an outer boundary with sides which meet at right angles. As seen in FIG. 4, notches 17 may be made progressively smaller as the distance from the base 12 to each notch 17 increases. The height of a particular slice which includes a notch 17, relative to base 12, may then be determined based on the actual dimensions of the notch or by knowing (via the working volume in the CT software) which notch is being used. The notches may also be used to ensure that the slice plane is parallel with the base 17, or orthogonal to the vertical axis of the pyramidal structure 11, whereby the radiographer ensures parallelism by adjusting the slice plane until each corner notch appears equally. The notches are also used for making external, ground truth determination of the actual dimensions of the notches at various locations via some other metrology tool. This is possible by virtue of the pyramid design having external facing features.

FIG. 7A shows a series of disc-shaped X-ray penetrameters of varying sizes, including a small penetrameter 20*c*, a medium-sized penetrameter 20*b*, and a large penetrameter 20*a*. Each pentameter has multiple holes therethrough of varying sizes, including at least a small hole 22 and a large hole 21. In various embodiments, the diameter of each hole 21 and each hole 22 may be a defined percentage of the diameter of the corresponding disc-shaped penetrameter. Thus, as the penetrameter diameter becomes smaller, the size of each hole 21 and each hole 22 becomes smaller. Disc-shaped X-ray penetrameters as shown in FIG. 7A may be prepared by laser micromachining.

FIG. 7B shows a stack 23 of disc-shaped members of varying diameters, arranged in a generally conical fashion. Stack 23 includes disc-shaped X-ray penetrameters 20*c*, 20*b*, and 20*a*. Stack 23 also includes additional disc-shaped members 20*d*, where disc-shaped members 20*d* may be solid discs, spacer discs having a CT opacity which differs from, e.g., is less than, that of penetrameter discs 20*a*-c, or additional disc-shaped penetrameters of varying sizes. Stack 23 includes a plurality of large and small holes 21 and 22. FIG. 7C shows a pyramidal structure 11 with stack 23 within conical bore 24.

When taking a CT scan of a pyramidal structure 11 with stack 23 within conical bore 24, a slice of the combined structure may be taken through one or more of discs 20*a*, 20*b*, and 20*c*, which each have at least one small hole 22 and at least one large hole 21 therethrough, as seen in FIG. 7B. Such slices may then be examined to see if holes 21 and 22 are detectable. The diameter of the smallest hole 21 or 22 that can be detected provides a measure of the contrast in a CT scan.

Thus, the grooves 15*a* to 15*d* of pyramidal structure 11, as seen in FIGS. 4 and 5, provide a way to measure resolution in a CT scan. Penetrameters positioned within conical bore 24 of pyramidal structure 11, as seen in FIG. 7C, provide a way to measure contrast in a CT scan. Either pyramidal structure 11 or a stack 23 containing penetrameters 20*a*-20*c* may be used to assess CT image quality. Pyramidal structure 11 and stack 23 may be used individually or in combination.

Various embodiments disclosed herein relate to a method of determining a resolution obtainable in a cross sectional image of a three-dimensional object obtained by computed tomography, by obtaining a series of cross sectional images of a pyramidal structure 11 having a base 12, an apex 14, and a plurality of triangular faces 13 extending from the base to the apex, each cross sectional image being along a plane parallel to the base 12. Each triangular face 13 has at least two grooves and a land 16 between each pair of adjacent grooves, e.g., two grooves 15*a* and a land 16 therebetween are on a first face 13*a*, with each groove tapering from a wide end at the base to a narrow end at the apex. The method involves observing the series of cross sectional images to determine a minimum resolvable groove width for the grooves on the triangular faces. In various embodiments, each groove tapers from a width of 0.5 mm to 4 mm at the wide end to a width of 0.005 mm to 0.5 mm at the narrow end, or 0.5 mm to 4 mm at the wide end to a width of 0.01 mm to 0.1 mm at the narrow end. The smallest resolvable groove width provides a measure of CT resolution.

Various embodiments disclosed herein relate to a method of determining a contrast obtainable in a cross sectional image of a three-dimensional object obtained by computed tomography, by obtaining a series of cross sectional images of a pyramidal structure having a bore and at least one disc-shaped penetrameter positioned within the bore, where the cross sectional images pass through the disc-shaped penetrameter. Each penetrameter may have a plurality of holes of varying sizes; and the series of cross sectional images are observed to determine the smallest penetrameter hole detectable to determine the minimum observable contrast.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A three-dimensional image quality indicator for X-ray Computed Tomography, comprising:

a pyramidal structure made of one of a plastic and metal material; said pyramidal structure having:

a base, an apex, and a plurality of triangular faces extending from the base to the apex, at least two grooves in each triangular face, each groove tapering from a wide end at the base to a narrow end at the apex; and a land between each pair of adjacent grooves in each triangular face, each land tapering from the base to the apex; wherein said indicator provides a structure to measure contrast and resolution of a CT scan when exposed to X-rays of said X-Ray Computed Tomography.

2. The three-dimensional image quality indicator of claim 1, wherein each groove has straight edges and a defined width at half-height.

3. The three-dimensional image quality indicator of claim 1, wherein:

each groove on a first triangular face has straight edges and a first defined width at half-height; and each triangular face which is adjacent to the first triangular face has grooves with straight edges and a second defined width at half-height;

the second defined width being different from the first width.

4. The three-dimensional image quality indicator of claim 3, wherein the pyramidal structure has an even number of triangular faces, the even number ranging from 4 to 8.

5. The three-dimensional image quality indicator of claim 3, wherein the pyramidal structure has 4 triangular faces.

6. The three-dimensional image quality indicator of claim 1, wherein:

each groove on each triangular face has straight edges and a defined width at half-height; and no two triangular faces have grooves with the same defined width at half-height.

7. The three-dimensional image quality indicator of claim 6, wherein the pyramidal structure has from 3 to 8 triangular faces.

8. The three-dimensional image quality indicator of claim 6, wherein the pyramidal structure has 4 triangular faces.

9. The three-dimensional image quality indicator of claim 1, wherein the pyramidal structure has a truncated apex with a flat or rounded surface.

10. The three-dimensional image quality indicator of claim 1, wherein the pyramidal structure has a pointed apex.

11. The three-dimensional image quality indicator of claim 1, further comprising a conical bore in the pyramidal structure, said conical bore having a first diameter at the base and a second diameter at the apex, the first diameter being greater than the second diameter.

12. The three-dimensional image quality indicator of claim 1, further comprising:

a conical bore in the pyramidal structure, said conical bore having a first diameter at the base and a second diameter at the apex; and a stack comprising a plurality of cylindrical members, the stack being configured to occupy the conical bore.

13. The three-dimensional image quality indicator of claim 12, wherein at least one of the cylindrical members has a plurality of holes therethrough.

14. The three-dimensional image quality indicator of claim 12, wherein at least one of the cylindrical members is a radiographic penetrameter having a plurality of holes of varying diameter therethrough.

15. The three-dimensional image quality indicator of claim 1, wherein a first pair of adjacent triangular faces contacts at a first edge, the first edge including a plurality of evenly spaced features.

16. The three-dimensional image quality indicator of claim 15, wherein the evenly spaced features are notches.

17. A method of determining a resolution obtainable in a cross sectional image of the three-dimensional image quality indicator of claim 1, said method comprising the steps of:

obtaining a series of cross sectional images of said pyramidal structure; and observing the series of cross sectional images to determine a minimum resolvable groove width for the grooves on the triangular faces.

18. The method of claim 17, wherein each groove tapers from a width of 0.5 mm to 4 mm at the wide end to a width of 0.005 mm to 0.5 mm at the narrow end.

19. The method of claim 17, wherein each groove is characterized in that a ratio of a width of the narrow end of the groove to a width of the wide end of the groove is between 1:10 and 1:100.

* * * * *